United States Patent
Shirvan et al.

(10) Patent No.: US 6,555,585 B2
(45) Date of Patent: Apr. 29, 2003

(54) USE OF DERIVATIVES OF VALPROIC ACID AND 2-VALPROENIC ACID AMIDES FOR THE TREATMENT OF MANIA IN BIPOLAR DISORDER

(75) Inventors: Mitchell Shirvan, Hertzleya (IL); Meir Bialer, Jerusalem (IL)

(73) Assignees: Teva Pharmaceutical Industries, Ltd., Petach-Tikva (IL); Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/910,543

(22) Filed: Jul. 20, 2001

(65) Prior Publication Data

US 2002/0103237 A1 Aug. 1, 2002

Related U.S. Application Data

(60) Provisional application No. 60/220,102, filed on Jul. 21, 2000.

(51) Int. Cl.$^7$ ............................................. A61K 31/16
(52) U.S. Cl. ........................................................ 514/616
(58) Field of Search ........................................ 514/616

(56) References Cited

U.S. PATENT DOCUMENTS

| | | | |
|---|---|---|---|
| 4,639,468 | A | 1/1987 | Roncucci et al. |
| 4,913,906 | A | 4/1990 | Friedman et al. |
| 5,585,358 | A | 12/1996 | Bialer et al. |
| 5,945,416 | A | 8/1999 | Shannon et al. |
| 6,251,946 | B1 | 6/2001 | Vinikova et al. |
| 6,268,396 | B1 | 7/2001 | Nau et al. |

FOREIGN PATENT DOCUMENTS

| | | |
|---|---|---|
| BE | 885303 | 9/1980 |
| CA | 1208230 | 7/1986 |
| EP | 0046707 | 3/1982 |
| EP | 0250997 | 7/1988 |
| EP | 0442012 | 8/1991 |
| EP | 0659174 | 10/1999 |
| FR | 2531950 | 8/1983 |
| GB | 2126224 | 3/1984 |
| SU | 988188 | 1/1983 |
| WO | WO 8801861 | 3/1988 |

OTHER PUBLICATIONS

The American Heritage Stedman's Medical Dictionary, 1995, Houghton Mifflin Company.*
Belmaker et al., "Perspectives for New Pharmacological Interventions", in *Basic Mechanisms and Therapeutic Implications*, Eds. S. Gershon and J. Soares, Marcel Dekker, Inc., New York, 2000, 507–527.
Bialer, "Clinical Pharmacology of Valpromide", *Clinical Pharmacokinet.*, 1991, 20(2) : 114–122.
Bialer et al., "Pharmacokinetics of a Valpromide Isomer, Valnoctamide, in Healthy Subjects", *Eur. J. Clin. Pharmacol.*, 1990, 38:289–291.
Bowden et al., "Efficacy of Divalproex vs Lithium and Placebo in the Treatment of Mania", *JAMA*, 1994, 271: 918–924.
Calabrese et al., "Lithium and the Anticonvulsants in the Treatment of Bipolar Disorder", *Psychopharmacology: The 4$^{th}$ Generation of Progress.*, Eds. R. Bloom and D. Kupfer, Raven Press, Ltd., New York, 1995, 1099–1111.
Granneman et al., "Aspects of the Metabolism of Valproic Acid", *Chem. Abstracts*, 1984, 101(17): 143458.
Granneman, "Aspects of the Metabolism of Valproic Acid", *Xenobiotica*, 1984, 14(5): 375–387.
Hadad et al., "Pharmacokinetic Analysis of Ester Prodrugs of Valproic Acid," *J. Pharm. Sci.*, 1992, 81(10): 1047–1050.
Haj-Yehia et al., "Structure–Pharmacokinetic Relationships in a Series of Valpromide Derivatives with Antiepileptic Activity", *Pharm. Research*, 1989, 6(8): 683–689.
March, Advanced Organic Chemistry, 3$^{rd}$ Edition, 1985, 354–355,368,377–379.
Yu et al., "Simultaneous Delivery of Valproic Acid and Glycine to the Brain", Mol. & Chem. Neuropath., 1991, 15(1): 37–49.
"Milacemide", *Drugs of the Future*, 1984, 9(8): 587–588 and "Milacemide", *Drugs of the Future*, 1991, 16(8): 775.

* cited by examiner

*Primary Examiner*—William R. A. Jarvis
(74) *Attorney, Agent, or Firm*—John P. White; Cooper & Dunham LLP

(57) ABSTRACT

A method for the treatment of mania in bipolar disorder using derivatives of valproic acid and 2-valproenic acid amides having the following structures:

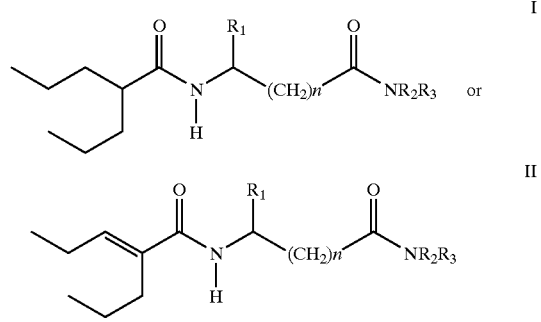

wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3, or a compound containing a valproic or a 2-valproenic moiety, as well as pharmaceutical compositions comprising these derivatives or compounds.

16 Claims, No Drawings

USE OF DERIVATIVES OF VALPROIC ACID AND 2-VALPROENIC ACID AMIDES FOR THE TREATMENT OF MANIA IN BIPOLAR DISORDER

This application claims the benefit of U.S. Provisional Application No. 60/220,102, filed Jul. 21, 2000.

Throughout this application, various references are referenced by short citations within parenthesis. Full citations for these references may be found at the end of the specification, immediately preceding the claims. These references, in their entireties, are hereby incorporated by reference to more fully describe the state of the art to which this invention pertains.

FIELD OF THE INVENTION

Disclosed is a method for the treatment of mania in bipolar disorder using derivatives of valproic acid and 2-valproenic acid amides.

BACKGROUND OF THE INVENTION

Affective disorders refer mainly to changes in mood rather than thought disturbances (Rang, H. P., M. M. Dale and J. M. Ritter). Depression is the most common manifestation, although it also includes mania. In many respects the symptoms of mania are opposite to those of depression. Whereas the symptoms of depression include a feeling of misery, apathy, and low self-esteem, those of mania include excessive exuberance, enthusiasm and self-confidence. There are two basic types of depressive syndrome: bipolar and unipolar (Rang, H. P., M. M. Dale and J. M. Ritter). Patients with a history of both depression and mania are considered to have a bipolar disorder (BPD). Those patients which suffer from depression are considered to be unipolar. Bipolar disorder is further subdivided into different segments. In bipolar I patients have at least one manic episode with or without depression. In bipolar II patients have at least one hypomanic episode with depression. Patients with BPD have the highest rate of suicide among patients with psychiatric illnesses.

Anti-depresants are the standard treatment for unipolar depression, but are not effective for mania. To treat mania in bipolar depression lithium ($Li^+$) has classically been used, and more recently the anti-epileptic drug (AED) valproate has been demonstrated to be effective (Bowden et al.; Calabrese, J. R. et al.) Other AEDs, such as carbamazepine, are also considered to be useful for mania. However phenobarbital, although clearly an effective AED, is not useful as a drug to treat mania (Belmaker, R. H. and Y. Yaroslavsky), or affective disorders. Today, many patients with mania are not controlled by current treatments (Calabresse, J. R. et al.). Therefore, there is a need for new treatments.

In order to discover new drugs in this area, rodent models relevant to the manic phase are used. One commonly used model is the amphetamine-induced hyperactivity model (Lyon, M.). This model focuses on an induced increase in the activity level of the animal (hyperactivity) as a parallel to the hyperactivity of the manic patient. The reversal of the induced hyperactivity in rodents, by pretreatment with a drug indicates the possible efficacy of this drug in the treatment of human mania. The most consistent finding with $Li^+$ (the standard drug for mania) in untreated animals, is the reduction in rearing (Johnson, F. N.). Rearing is followed in the models by observing the vertical activity of the animals.

Bialer et al. describe a series of derivatives of valproic acid amides and 2-valproenic acid for the effective treatment of epilepsy and other neurological disorders (U.S. Pat. No. 5,585,358).

SUMMARY OF THE INVENTION

It has been surprisingly observed that the valproic acid amide of Bialer et al. (U.S. Pat. No. 5,585,358), Compound 1 below, decreases amphetamine-induced hyperactivity. The subject invention provides a method for the treatment of mania in bipolar disorder using derivatives of valproic acid amides and 2-valproenic acid amides.

The subject invention provides a method of treating mania in bipolar disorders in a subject. The invention comprises the administration of a therapeutically effective amount of a derivative of a valproic acid amide or a 2-valproenic acid amide having one of the following structures:

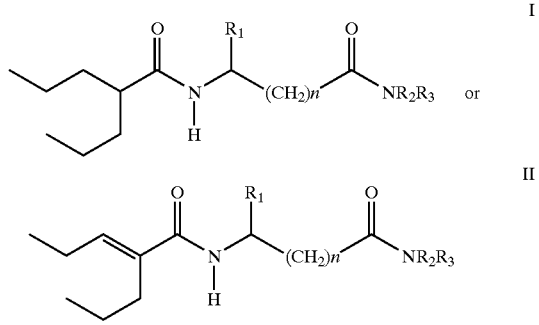

wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3, or a compound containing a valproic or a 2-valproenic moiety, as well as pharmaceutical compositions comprising these derivatives or compounds.

DETAILED DESCRIPTION OF THE INVENTION

Disclosed is a method of treating bipolar disorder in a subject comprising administering to the subject a therapeutically effective amount of a derivative of a valproic acid amide or a 2-valproenic acid amide having one of the following structures:

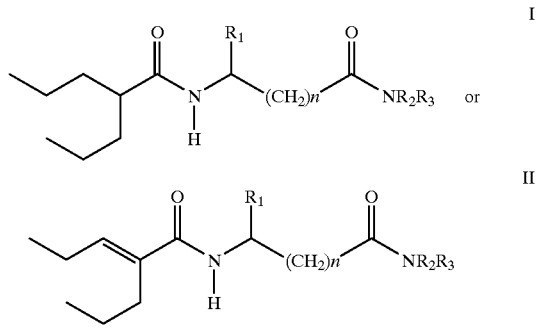

wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3, to thereby treat the bipolar disorder.

The derivative may have the structure:

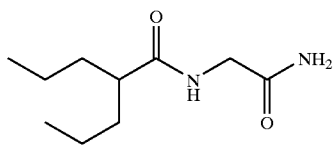

The derivative used in the method may be in the form of a pharmaceutical composition with a pharmaceutically acceptable carrier. The derivative may also be in the form of a pharmaceutically acceptable salt.

The bipolar disorder may be mania.

The subject may be human.

In one embodiment, the invention provides the derivative of formula I hereinabove shown wherein the $C_1-C_6$ alkyl group is a linear chain alkyl group. In another embodiment, the invention provides the derivative of formula I hereinabove shown wherein the $C_1-C_6$ alkyl group is a branched chain alkyl group. In yet another embodiment, the invention provides the derivative of formula I hereinabove shown wherein the aralkyl group is a benzyl, alkylbenzyl, hydroxybenzyl, alkoxycarbonylbenzyl, aryloxycarbonylbenzyl, carboxybenzyl, nitrobenzyl, cyanobenzyl, or halobenzyl group. In still another embodiment, the invention provides the derivative of formula I wherein the aryl group is a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, or aminophenyl group.

In one embodiment, the invention provides the derivative of formula II hereinabove shown wherein the $C_1-C_6$ alkyl group is a linear chain alkyl group. In another embodiment, the invention provides the derivative of formula II hereinabove shown wherein the $C_1-C_6$ alkyl group is a branched chain alkyl group. In still another embodiment, the invention provides the derivative of formula II hereinabove shown wherein the aralkyl group is a benzyl, alkylbenzyl, hydroxybenzyl, alkoxycarbonylbenzyl, aryloxycarbonylbenzyl, carboxybenzyl, nitrobenzyl, cyanobenzyl, or halobenzyl group. In yet another embodiment, the invention provides the derivative of formula II hereinabove shown wherein the aryl group is a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, or aminophenyl group.

Some of the derivatives used in this invention possess chiral centers. It is a further embodiment of this invention that these derivatives may comprise substantially pure D or L enantiomers or racemic mixtures. It is to be understood that derivatives of the general formula II may be of the E-(trans) or Z-(cis) geometric configuration, or a mixture thereof.

In the practice of the invention, the amount of the derivative incorporated in the pharmaceutical composition may vary widely. Factors considered when determining the precise amount are well known to those skilled in the art. Examples of such factors include, but are not limited to, the subject being treated, the specific pharmaceutical carrier, and route of administration being employed and the frequency with which the composition is to be administered.

In one embodiment, the effective amount of derivatives of valproic acid amides and 2-valproenic acid amides for the treatment of mania in bipolar disorder comprises an amount from about 10 to about 1,000 mg. The effective amount may also be an amount from about 10 mg to about 500 mg. Additionally, the effective amount may comprise an amount from about 50 mg to about 500. The effective amount may additionally comprise an amount from about 100 mg to about 250 mg. Also, the effective amount may comprise an amount from about 150 mg to about 200 mg.

In a preferred embodiment, the derivative is administered in a pharmaceutical composition which comprises the derivative and a pharmaceutically acceptable carrier. As used herein, the term "pharmaceutically acceptable carrier" encompasses any of the standard pharmaceutically accepted carriers, such as a phosphate-buffered saline solution, water, emulsions such as an oil/water emulsion or a triglyceride emulsion, various types of wetting agents, tablets, coated tablets, and capsules. An example of an acceptable triglyceride emulsion useful in the intravenous and intraperitoneal administration of the derivatives is the triglyceride emulsion commercially known as Intralipid®.

Typically, such carriers contain excipients such as starch, milk, sugar, certain types of clay, gelatin, stearic acid, talc, vegetable fats or oils, gums, glycols, or other known excipients. Such carriers may also include flavor and color additives or other ingredients.

In the practice of the invention, the administration of the pharmaceutical composition may be effected by any of the well known methods including, but not limited to, rectal, oral, intravenous, intraperitoneal, parenteral, intramuscular, transmdermal, subcutaneous or topical administration. Topical administration can be effected by any method commonly known to those skilled in the art and include, but are not limited to, incorporation of the pharmaceutical composition into creams, ointments, or transdermal patches.

The invention further provides a pharmaceutical composition which comprises any derivative of Formula I or II in a amount which is therapeutically effective to treat mania in bipolar disorder and a pharmaceutically acceptable carrier. The invention encompasses a pharmaceutical composition as hereinabove described wherein the carrier is a solid and the composition is a tablet. The invention also encompasses a pharmaceutical composition as hereinabove described wherein the carrier is a gel and the composition is a suppository. The invention further encompasses a pharmaceutical composition as hereinabove described wherein the carrier is a liquid and the composition is a solution.

The following Experimental Details are set forth to aid in an understanding of the invention, and are not intended, and should not be construed, to limit in any way the invention set forth in the claims which follow thereafter.

Experimental Details

I. Synthesis of Compound 1

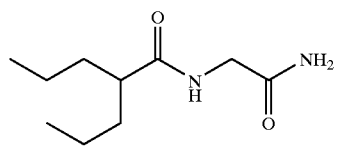

Compound 1

Compound 1 was prepared as disclosed by Bialer et al. (U.S. Pat. No. 5,585,358).

II. Experimental Examples

Evaluation of possible anti-bipolar effects of Compound 1 was followed in the amphetamine-induced hyperactivity model of mania in rats. Activities of rats were followed in an activity meter (Elvicom, Israel) based on 2 levels laser beams and equipped with a computerized system that can count the vertical movements of rats (rearing). Activities were recorded for ~30 min for each session, and the resultant appropriate movement reported per 30 min. Rats were housed under a 12 hr light/dark cycle and the behavioral testing was conducted in the light phase.

The activities of rats following treatment with Compound 1, Li⁺ (the standard drug for mania), and a control group were followed before and after being challenged with amphetamine. The statistical analyses were conducted using a two way ANOVA for the effects of drugs, amphetamine (repeated measure) and the drug-amphetamine interaction.

In these experiments 30 male Sprague Dawley (weighing 200–250 g) rats were equally divided into 3 treatment groups: control, Li⁺ (6 mg/kg by gavage)), and Compound 1 (200 mg/kg by gavage) (Drugs were suspended in 5% methyl cellulose). Half of the rats in each group were challenged (administered) amphetamine (0.5 mg/kg subsutaneously (s.c.)) and the other half was given saline (s.c.). Ten minutes later all rats were placed in the activity meter. One week later the procedure was repeated, except that the order of treatment was reversed; those rats which received saline on the first day were given amphetamine and those given amphetamine the first day were administered saline.

III. Results

The results of the experiment employing Compound 1 are shown in Table 1. Hyperactivity in the rats was induced after the amphetamine challenge, as indicated by the increase in rearing (vertical movements) compared to saline challenged animals in the control group.

Treatment with Compound 1 reduced the rearing when animal were challenged with amphetamine compared to control animals challenged with atmphetamine (p=0.06) (Table 1). This effect is in a similar direction to that observed with Li⁺.

TABLE 1

Activities of rats on Compound 1 or Li⁺ after a challenge with saline or amphetamine.

| Challenge | Saline Mean activity | SD | Amphetamine Mean Activity | SD |
|---|---|---|---|---|
| Vertical Activity (Rearing) Treatments | | | | |
| Control | 102.9 | 83.7 | 181.4 | 138.3 |
| Li | 59.8 | 45 | 126.7 | 173.1 |
| Compound 1 | 34.1 | 26 | 71.3 | 49.4 |

SD, standard deviation

Discussion

The effects of Compound 1 in rats have been evaluated in comparison with that of Li⁺, a well established drug for the treatment of bipolar disease. Compound 1 was tested in the amphetamine-induced hyperactivity model, that is well accepted as a model of bipolar disease (mania phase). The end point criteria was reduction in vertical movements (rearing). Compound 1 decreased the induced rearing in a similar manner as Li⁺, indicating that Compound 1 and the claimed valproic acid amides and 2-valproenic acid amides are effective for the treatment of mania in bipolar disorder.

References

U.S. Pat. No. 5,585,358, Bialer et al., issued Dec. 6, 1996.

Belmaker, R. H. and Y. Yaroslavsky, Basic Mechanism and Therapeutic Implications of BP disorder, Marcel Dekker, Inc., Ed. S. Gershon and J. Soares, 2000.

Bowden et al., Efficacy of divalproex vs. lithium and placebo in the treatment of mania, JAMA 1994: 271:918–924.

Calabrese, J. R. et al., Lithium and the anticonvulsants in the treatment of bipolar disorder, in: Psychopharmacology: The fourth generation of progress, eds. R. Bloom and D. Kupfer, Raven Press, Ltd., 1995.

Lyon, M., Animal model mania and schizophrenia in: Willner, P. Behavior Model in Psychopharmacology, Cambrige University Press, NY, 1991, pp. 253–310.

Johnson, F. N., Association of vertical and horizontal components of activity in rats treated with lithium chloride, Experientia, 1972, 28: 533–535.

Rang, H. P., M. M. Dale and J. M. Ritter, Pharmacology 3$^{rd}$ Ed., Churchill Livingstone, p. 576.

What is claimed:

1. A method of treating the mania phase of bipolar disorder in a subject comprising administering to the subject a therapeutically effective amount of a derivative of a vaiproic acid amide or a 2-valproenic acid amide having one of the following structures:

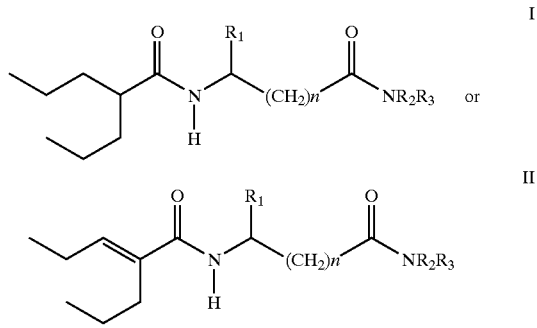

wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3, to thereby treat the mania phase of bipolar disorder.

2. The method of claim 1, wherein the derivative has the structure:

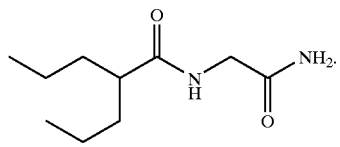

3. The method of claim 1, wherein the derivative is in a pharmaceutical composition with a pharmaceutically acceptable carrier.

4. The method of claim 1, wherein the derivative is in the form of a pharmaceutically acceptable salt.

5. The method of claim 1, wherein the subject is human.

6. The method of claim 1, wherein the route of administration is selected from the group consisting of oral, parenteral, intraperitoneal, intravenous, intramuscular, transdermal, subcutaneous, topical and rectal administration.

7. The method of claim 1, wherein the effective amount is an amount from about 10 mg to 1,000 mg.

8. The method of claim 7, wherein the effective amount is an amount from about 50 mg to 500 mg.

9. The method of claim 1, wherein the derivative has structure I and the $C_1$–$C_6$ alkyl group is a linear chain alkyl group.

10. The method of claim 1, wherein the derivative has structure I and the $C_1$–$C_6$ alkyl group is a branched chain alkyl group.

11. The method of claim 1, wherein the derivative has structure I and the aralkyl group is selected from the group consisting of a benzyl, alkylbenzyl, hydroxybenzyl, alkoxycarbonylbenzyl, aryloxycarbonylbenzyl, carboxybenzyl, nitrobenzyl, cyanobenzyl, and halobenzyl group.

12. The method of claim 1, wherein the derivative has structure I and the aryl group is selected from the group consisting of a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, and aminophenyl group.

13. The method of claim 1, wherein the derivative has structure II and the $C_1$–$C_6$ alkyl group is a linear chain alkyl group.

14. The method of claim 1, wherein the derivative has structure II and the $C_1$–$C_6$ alkyl group is a branched chain alkyl group.

15. The method of claim 1, wherein the derivative has structure II and the aralkyl group is selected from the group consisting of a benzyl, alkylbenzyl, hydroxybenzyl, alkoxycarbonylbenzyl, aryloxycarbonylbenzyl, carboxybenzyl, nitrobenzyl, cyanobenzyl, and halobenzyl group.

16. The method of claim 1, wherein the derivative has structure II and the aryl group is selected from the group consisting of a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, and aminophenyl group.

* * * * *